(12) United States Patent
Sohm et al.

(10) Patent No.: US 9,538,750 B2
(45) Date of Patent: Jan. 10, 2017

(54) SOLID HERBICIDAL COMPOSITION COMPRISING MESOTRIONE

(75) Inventors: Rupert Heinrich Sohm, Munchwilen (CH); Christian Krueger, Basel (CH); Flavio Castagnini, Muenchwilen (CH); Mario Antenucci, Muenchwilen (CH)

(73) Assignee: Syngenta Participations AG, Basel (CH)

(*) Notice: Subject to any disclaimer, the term of this patent is extended or adjusted under 35 U.S.C. 154(b) by 27 days.

(21) Appl. No.: 14/004,593

(22) PCT Filed: Mar. 8, 2012

(86) PCT No.: PCT/EP2012/053958
§ 371 (c)(1),
(2), (4) Date: Sep. 11, 2013

(87) PCT Pub. No.: WO2012/123314
PCT Pub. Date: Sep. 20, 2012

(65) Prior Publication Data
US 2014/0005050 A1 Jan. 2, 2014

(30) Foreign Application Priority Data
Mar. 11, 2011 (GB) .................................. 1104204.1

(51) Int. Cl.
| *A01N 47/10* | (2006.01) |
| *A01N 25/30* | (2006.01) |
| *A01N 25/14* | (2006.01) |
| *A01N 25/22* | (2006.01) |
| *A01N 37/36* | (2006.01) |
| *A01N 59/26* | (2006.01) |
| *A01N 47/36* | (2006.01) |
| *A01N 43/647* | (2006.01) |
| *A01N 43/653* | (2006.01) |
| *A01N 43/66* | (2006.01) |
| *A01N 43/68* | (2006.01) |
| *A01N 43/70* | (2006.01) |
| *A01N 43/707* | (2006.01) |
| *A01N 41/10* | (2006.01) |

(52) U.S. Cl.
CPC .............. *A01N 41/10* (2013.01); *A01N 25/14* (2013.01); *A01N 25/22* (2013.01); *A01N 25/30* (2013.01); *A01N 37/36* (2013.01); *A01N 43/647* (2013.01); *A01N 43/653* (2013.01); *A01N 43/66* (2013.01); *A01N 43/68* (2013.01); *A01N 43/70* (2013.01); *A01N 43/707* (2013.01); *A01N 47/36* (2013.01); *A01N 59/26* (2013.01)

(58) Field of Classification Search
CPC ........ A01N 41/10; A01N 25/30; A01N 25/22; A01N 25/14; A01N 37/36; A01N 59/26; A01N 47/36; A01N 43/647; A01N 43/653; A01N 43/66; A01N 43/68; A01N 43/70; A01N 43/707
See application file for complete search history.

(56) References Cited

U.S. PATENT DOCUMENTS

| 6,551,964 | B1 * | 4/2003 | Bardsley | ................ A01N 25/30 504/358 |
| 2007/0021305 | A1 * | 1/2007 | Baker | .................... A01N 25/26 504/348 |
| 2007/0207929 | A1 * | 9/2007 | Reynolds et al. | ............ 504/191 |
| 2007/0232492 | A1 * | 10/2007 | Kikugawa | .............. A01N 47/36 504/118 |
| 2009/0069346 | A1 * | 3/2009 | Ishihara et al. | ............... 514/256 |

FOREIGN PATENT DOCUMENTS

| GB | WO 02/063956 A1 * | 8/2002 | ............. A01N 25/04 |
| WO | 2007101620 | 9/2007 | |
| WO | 2007105377 | 9/2007 | |

OTHER PUBLICATIONS

J.S. Dyson, S. Beulke, C. D. Brown and M. C. G. Lane, "Adsorption and Degradation of the Weak Acid Mesotrione in Soil and Environmental Fate Implications", Journal of Environmental Quality, 31(2), 613-618 (2002), Abstract only.*
International Search Report, International Application No. PCT/EP2012/53958, completion date Jun. 19, 2012.

* cited by examiner

*Primary Examiner* — John Pak
*Assistant Examiner* — Nathan W Schlientz
(74) *Attorney, Agent, or Firm* — James Cueva

(57) ABSTRACT

The present invention relates to a solid herbicidal composition comprising: i. mesotrione; ii. at least one arene sulfonate condensed with formaldehyde (e.g. sodium alkylnaphthalene sulfonate condensed with formaldehyde); and iii. an acidifying agent. The present invention further provides a method of controlling weeds at a locus comprising diluting the solid herbicidal composition of the present invention and applying to the locus a weed controlling amount of the diluted herbicidal composition.

4 Claims, No Drawings

SOLID HERBICIDAL COMPOSITION COMPRISING MESOTRIONE

This application is a 371 of International Application No. PCT/EP2012/053958 filed Mar. 8, 2012, which claims priority to GB 1104204.1, filed Mar. 11, 2011, the contents of which are incorporated herein by reference.

The present invention relates to the provision of a chemically stable solid herbicidal composition comprising the herbicide mesotrione. Solid herbicidal compositions comprising mesotrione are known in the art. For example, WO 2008/014185 teaches controlled release granules comprising mesotrione; WO 2007/133522 teaches granules comprising mesotrione and diuron. However, it has now been discovered that the mesotrione, in its acid form, can exhibit relatively poor chemical stability in such solid compositions. Thus, the present invention provides improved solid mesotrione compositions in which the chemical stability is significantly improved. This improvement is achieved via the use of a certain specific arene sulfonate condensate surfactants. It has also been discovered that the stability can be improved still further by the inclusion of an acidifying agent into the composition. Arene sulfonate condensates are known in the context of solid herbicidal compositions. For example, US2009/0069346 discloses the use of such compounds to reduce the decomposition of the sulfonyl urea herbicide flazasulfuron in a solid herbicidal composition. The present invention is based, in part, on the surprising discovery that these compounds are able to chemically stabilise the chemically unrelated herbicide mesotrione in solid formulations.

Thus, according to the present invention there is provided a solid herbicidal composition comprising:
  i. mesotrione;
  ii. at least one arene sulfonate condensed with formaldehyde; and
  iii. an acidifying agent.

Solid herbicidal compositions include, for example, dusts, powders (including wettable powders and water soluble powders), wettable granules (including extruded granules, water dispersible granules, water soluble granules, spray dried granules, fluid bed granules and tablets. Such solid composition types and corresponding manufacturing methods (extrusion, compaction, fluid bed granulation, spray-dried granulation etc) are well known to the skilled formulation chemist.

Mesotrione (2-[4-(methylsulfonyl)-2-nitrobenzoyl]-1,3-cyclohexanedione) is a herbicidal compound disclosed in EP-A-186118. The mesotrione is present in the solid composition in its "acid" form. The exact concentration of mesotrione in the solid composition will be dictated by, for example, factors such as the solid formulation type, intended purpose and the presence of other active ingredients in the composition. Thus the, the mesotrione may be present from 0.01% to 90% w/w. Typically, the mesotrione will be present from 0.1% to 60%, more preferably from 1% to 50% w/w. It is further known that mesotrione can exist in several crystalline polymorphs, for example as disclosed in WO06/021743 and WO2011/016018. Whilst it is possible that any of the polymorphs may be used in the context of the solid composition of the present invention, it is preferred that the mesotrione be in the thermodynamically stable form 1.

In the context of "arene sulfonate" the term "arene" is taken to include, for example, naphthalene, phenol and cresol. The arene may also be optionally substituted by at least one "alkyl" giving rise to an "alkylarene". It should be understood that the arene may be mono-, di- or poly-substituted. In this context the term "alkyl" includes primary, secondary and tertiary alkyls. In a preferred embodiment the alkyl is a $C_1$ to $C_{12}$ alkyl, examples of which include methyl, ethyl, propyl, butyl, isopropyl, pentyl, hexyl, heptyl, octyl, nonyl, decyl, undecyl and dodecyl. In a particularly preferred embodiment of the present invention the arene sulfonate is a naphthalene sulfonate condensed with formaldehyde or a salt thereof as shown in Formula I.

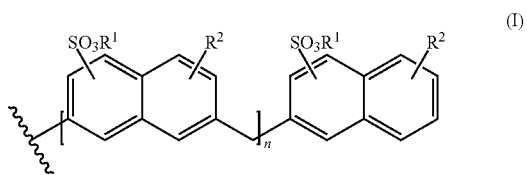

wherein
$R^1$ is independently hydrogen, an alkali metal, an alkaline earth metal, ammonium, a mono-, di-, or tri-$C_1$-$C_4$ alkyl-ammonium or a mono-, di- or tri-$C_1$-$C_4$ hydroxy-alkyl ammonium moiety;
$R^2$ is independently hydrogen, a $C_1$-$C_{30}$ straight or branched chain alkyl, or alkenyl group and can be present in any position, and in multiple positions, on the naphthalene moiety.
The n groups show the repetition of the monomer units. Each n is on average from 1-25.
As can be seen for the above, the naphthalene sulfonate condensed with formaldehyde may also provided in the form of a salt, and examples of suitable salts include alkali metal salts such as sodium, potassium and alkaline earth metal salts such as magnesium and calcium, salts of amines such as monomethylamine, dimethylamine and triethylamine. Sodium salts are particularly preferred. Examples of commercially available sodium salts of naphthalene sulfonates condensed with formaldehyde include Tersperse™ 2001, Tersperse™ 2100, Tersperse™ 2105 and Tersperse™ 2158 available from Huntsman, Tamol™ NH, NN range available from BASF. Salts of other arene sulfonates condensed with formaldehyde include sodium salt of phenol condensed with formaldehyde (Tamol™ PP, DN range available from BASF), sodium salt of cresol condensed with formaldehyde (Dispersogen™ 1494 and Rapidaminreserve™ CL available from Clariant).

It can also be seen that the naphthalene sulfonate condensed with formaldehyde—when $R^2=C_1$-$C_6$ alkyl, can be provided as an "alkyl" naphthalene sulfonate condensed with formaldehyde. Examples of suitable alkyl groups thus include methyl, ethyl, isopropyl, n-butyl and sec-butyl. Alkylnaphthalene sulfonates are particularly preferred in the context of the present invention and thus, in a preferred embodiment, the arene sulfonate condensed with formaldehyde is a sodium salt of alkylnaphthalene condensed with formaldehyde having a mean molecular weight of 300 to 2,000, preferably 400 to 1,000 and most preferably from 500 to 750. Examples of sodium salts of alkylnaphthalene condensed with formaldehyde which are available commercially include Morwet™ D-425, Morwet™ D-400, Morwet™ D-809 available from AkzoNobel; Tersperse™ 2425 and Tersperse™ 2020 available from Huntsman; and Supragil™ MNS-90 and MNS-425 available from Rhodia. Again, the concentration of the dispersant in the composition can vary depending, for example, on the exact physical nature of the composition. Typically, the dispersant will be present from 0.1% to 40% w/w, more preferably from 1% to 25% w/w, even more preferably from 2.5% to 10% w/w.

The solid herbicidal composition of the present invention is effectively a concentrate which will be diluted in an aqueous environment prior to use. The acidifying agent is thus present in the solid composition at a concentration which provides a pH from 2 to 6, more preferably from 2.5 to 5 with regard to the diluted solid herbicidal composition. Thus, it can be appreciated that the actual nature of the acidifying agent is not germane to the invention—indeed a broad range of solid and/or liquid acids could be utilised. Particularly suitable, non-limiting, examples include citric acid, tartaric acid, oxalic acid, malonic acid, fumaric acid, lactic acid and phosphoric acid. Additional active ingredients which themselves are acidic in nature may also act as acidifying agents, examples of which include dicamba, 2,4-D, glyphosate and glufosinate. In a particularly preferred embodiment the acidifying agent is citric acid. Furthermore, it can be appreciated that the actual concentration of acidifying agent in the solid herbicidal composition can vary—depending on the nature of, for example, the other components in the composition, and the diluents being used. Typically, the acidifying agent will be present from 0.01% w/w to 15% w/w, more preferably from 0.5% w/w to 5% w/w.

The solid herbicidal composition may further comprise an inert carrier, examples of which include, but are not limited to, mineral earths such as silicas, silica gels, silicates, talc, kaolin, attaclay, limestone, chalk, loess, clay, dolomite, bentonite, diatomaceous earth, calcium carbonate, brick, pumice, pyrophyllite, potassium chloride, magnesia, mica, iron oxide, zinc oxide, titanium oxide, antimony oxide, cryolite, vermiculite calcinated lime, gypsum, perlite, plaster, calcium sulphate, starch, talc, ground corn cobs, ground peanut hulls, sugars (as lactose or fructose), zeolithes, sodium chloride, sodium sulphate, sodium silicate, sodium borate, sodium carbonate, sodium bicarbonate magnesium sulphate, calcium sulphate, magnesium oxide, ground synthetic materials, fertilizers such as ammonium sulphate, ammonium hydrogensulphate, ammonium phosphate, ammonium nitrate, thiourea and urea, products of vegetable origin such as cereal meals, tree bark meal, wood meal and nutshell meal, cellulose powders, attapulgites, montmorillonites, micas, vermiculites, synthetic silicas and synthetic calcium silicates, and mixtures thereof. Suitably, the filler may be present in the solid composition from 1% to 90% w/w.

The solid herbicidal composition of the present invention may also contain various optional ingredients known to persons skilled in the art. For example, auxiliaries such as binders, adjuvants, rewetting agents, disintegration aids, de-dusting agents, stabilisers, surfactants, dyes and similar optional ingredients can be included. Surfactants customarily employed in formulation technology are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich, 1981 and M. and J. Ash, "Encyclopaedia of Surfactants", Vol I-III, Chemical Publishing Co., New York, 1980-81. Furthermore, other pesticides (e.g. herbicides, insecticides, fungicides, growth regulators) and/or herbicide safeners can also be present on or within the solid herbicidal composition. Thus, in one aspect of the invention the herbicidal composition further comprises one or more additional herbicides selected from the group consisting of sulfonylurea herbicides (e.g. amidosulfuron, bensulfuron-methyl, chlorimuron-ethyl, chlorsulfuron, cinosulfuron, flazasulfuron, flupyrsulfuron-methyl-sodium), formasulfuron, halosulfuron-methyl, iodosulfuron-methyl-sodium, nicosulfuron, primisulfuron-methyl, prosulfuron, rimsulfuron, triasulfuron, trifloxysulfuron-sodium and tritosulfuron), triazine herbicides e.g. (ametryn, atrazine, cyanazine, prometryn, simazine and terbuthylazine) and auxin herbicides (e.g. dicamba, 2,4-D) or an agrochemically acceptable salt thereof.

In a particularly preferred embodiment the solid herbicidal composition is an extruded granule. Such granules typically have a particle size in the range of about 0.1 to about 30 mm, particularly between about 0.25 to about 20 mm, and more particularly between about 0.5 to about 15 mm. In another embodiment the solid composition is produced by spray dried or fluid bed granulation.

As mentioned, the solid herbicidal composition of the present invention will be diluted prior to use. Typically, this dilution will take place in a "spray tank"—wherein further components may be added (e.g. fertilizers, other pesticides, water conditioners, adjuvants etc). A weed controlling amount of the diluted product will then be applied to a locus.

Thus, the present invention still further provides a method of controlling weeds at a locus comprising:

(i) diluting the solid herbicidal composition of the present invention;
(ii) applying to the locus a weed controlling amount of the diluted herbicidal composition.

The skilled person will appreciate that the term "weed controlling amount" will vary and will depend on, for example, the nature of the weeds to be controlled, the timing of the application and the environmental conditions. Typically, a "weed controlling amount" will be from 50 to 500 g/ha mesotrione. The term "locus" is taken to mean any place where weeds may grow—typically a field. The locus may also comprise crop plants, for example corn, sugar cane and/or soybean plants, where necessary the crop plant being modified to be resistant to the herbicidal composition being applied. The diluted herbicidal composition may be applied to the locus as a pre-emergence application (i.e. before the majority of the weeds emerge from the soil) and/or as a post-emergence application (i.e. after the majority of the weeds emerge from the soil).

EXAMPLES

A comparative experiment is performed to show the advantage that the solid herbicidal composition of the present invention has compared to those reported in the art (e.g. WO2007/133522). Water dispersible granules (WDG) are prepared according to the information provided in the table below. The WDGs are then stored in a thermostatic oven at a given temperature for a given time period (information provided in table). The content of Mesotrione in the water dispersible granules before and after the storage is quantitatively determined by liquid chromatography, and the decomposition rate of each water dispersible granules is calculated from the following formula to evaluate the change with time. The results obtained are shown in the table below.

Decomposition rate (%)={$(X-Y)/X$}×100

X: content immediately after preparation
Y: content after storage

Example 1

| Component | Comp* | A | B | C |
|---|---|---|---|---|
| Mesotrione | 5 | 5 | 5 | 5 |
| Anhydrous sodium sulfate | 30 | 30 | 30 | 30 |
| Calcium lignosulfonate | 5 | / | 5 | / |
| Sodium alkylnaphtalenesulfonate (Morwet™ IP) | 1 | 1 | 1 | 1 |
| Calcium bentonite | 59 | 59 | 57 | 57 |
| Sodium alkylnaphthalene sulfonate condensate (Morwet™ D-425) | 0 | 5 | 0 | 5 |
| Citric acid | 0 | 0 | 2 | 2 |
|  | 100 | 100 | 100 | 100 |
| pH (1% in water) | 4.0 | 4.0 | 3.5 | 3.5 |
| % w/w Mesotrione loss (2 w@54° C.) | 15.7 | 7.8 | 4.6 | 2.8 |

*"Comp" granule relates to one similar to that disclosed in WO2007/133522.

These results show that mesotrione is significantly more chemically stable in granules containing the alkylnaphthalene sulfonate condensed with formaldehyde.

Example 2

In this example other active ingredients belonging here to sulfonylurea class are introduced to the composition. The content of mesotrione in the water dispersible granules before and after the storage is determined by using the analytical method described above.

A "fluid bed granule" is prepared according to the following recipe. An aqueous slurry containing the ingredients described below is ground in a bead mill and sprayed into a granulation tower where suspension is dried by injecting warm air.

| Component | D % (w/w) | E % (w/w) |
|---|---|---|
| Mesotrione | 45 | 45 |
| Prosulfuron | 4.5 | 4.5 |
| Nicosulfuron | 9 | 9 |
| Sodium lignosulfonate | 20 | — |
| Sodium salt of alkylnaphthalene sulfonate condensate (Morwet™ D-425) | — | 20 |
| Citric acid | 2 | 0 |
| Aluminium silicate | Remainder | Remainder |
| pH (1% solution in water) | 3.8 | 3.5 |
| % w/w Mesotrione loss after 3 months@45° C. | 13% | 2% |

These results demonstrate that an alkylnaphthalene sulfonate condensed with formaldehyde improves the chemical stability of mesotrione in granule produced with fluid-bed technology and containing more than one herbicidal compound.

The invention claimed is:

1. A solid herbicidal composition comprising:
   i. from 1% to 50% w/w of mesotrione;
   ii. from 1% to 25% w/w of at least one alkylnaphthalene sulfonate condensed with formaldehyde; and
   iii. from 0.5% to 5% of an acidifying agent selected from the group consisting of citric acid, phosphoric acid and mixtures thereof.

2. The solid herbicidal composition according to claim 1, which is a wettable granule.

3. The solid herbicidal composition according to claim 1, which further comprises at least one additional herbicide selected from the group consisting of sulfonylurea herbicides, triazine herbicides and auxin herbicides.

4. The solid herbicidal composition according to claim 1, wherein the at least one alkylnaphthalene sulfonate condensed with formaldehyde is present in an amount from 2.5% to 10% w/w.

* * * * *